US007806852B1

(12) United States Patent
Jurson

(10) Patent No.: US 7,806,852 B1
(45) Date of Patent: Oct. 5, 2010

(54) METHOD AND APPARATUS FOR PATIENT-CONTROLLED MEDICAL THERAPEUTICS

(76) Inventor: Phillip A. Jurson, 2666 Vallego St., San Francisco, CA (US) 94123

( * ) Notice: Subject to any disclaimer, the term of this patent is extended or adjusted under 35 U.S.C. 154(b) by 3 days.

(21) Appl. No.: 11/396,847

(22) Filed: Apr. 3, 2006

(51) Int. Cl.
*A61M 31/00* (2006.01)

(52) U.S. Cl. .................. 604/65; 604/67; 604/890.1; 604/151

(58) Field of Classification Search ............ 604/131, 604/67, 890.1, 891.1, 65, 151–155; 283/68, 283/78; 382/115, 124, 126; 340/5.8, 5.83
See application file for complete search history.

(56) References Cited

U.S. PATENT DOCUMENTS

| 5,232,448 | A | 8/1993 | Zdeb ................... 604/153 |
| 6,807,965 | B1 | 10/2004 | Hickle .................. 128/204.23 |
| 6,899,695 | B2 | 5/2005 | Herrera ................. 604/65 |
| 7,526,111 | B2 * | 4/2009 | Miura et al. ............. 382/126 |
| 2003/0052135 | A1 * | 3/2003 | Conley ................. 221/258 |
| 2003/0233069 | A1 * | 12/2003 | Gillespie et al. ........... 604/131 |
| 2004/0039257 | A1 * | 2/2004 | Hickle ................. 600/300 |
| 2007/0156282 | A1 * | 7/2007 | Dunn .................. 700/244 |

OTHER PUBLICATIONS

"Abbott Laboratories Introduces the Lifecare® PCA3 Infusion System The-Art Patient-Controlled Analgesia Device," Hospira, Press Release, Retrieved from the Internet: <URL: http://www.hospira.com/NewsAndMediaCenter/e69e5681__2fe2__4b7c__83fc__ae84a8cd031...>, retrieved Mar. 22, 2005.
"Abbott Laboratories Introduces the LifeCare® PCA3 Infusion System, a State-of-the-art Patient-controlled Analgesia Device," Abbott Laboratories Press Releases (551). Retrieved from the Internet: <URL: http://abbott.com/news/releaseonly.cfm?id=551>, retrieved Mar. 22, 2005.
"Baxter Announces Launch of Syndeo Patient-Controlled Analgesia Syringe Pump," Baxter, News Release. Retrieved from the Internet: <URL: http://www.baxter.com/about__baxter/news__releases/2003/10-14-03-syndeo__p...>, Mar. 22, 2005.

(Continued)

*Primary Examiner*—Kevin C Sirmons
*Assistant Examiner*—Laura C Schell
(74) *Attorney, Agent, or Firm*—McDonnell Boehnan Hulbert & Berghoff LLP

(57) ABSTRACT

An apparatus and associated methods are provided to authenticate a patient based on a biometric identifier of the patient before a prescribed dose of medical therapeutic, such as analgesics or other medication, are dispensed to the patient. Authentication takes places by pressing a button and scanning the patient's fingerprint and recording data corresponding to the fingerprint into memory. To receive the medical therapeutic, the patient can have his or her fingerprint read and compared to the stored fingerprint. If there is a match and the programmed limitations are met (e.g., a time interval has elapsed since the last dose), then the medical therapeutic is automatically dispensed to the patient. The system may be integrated with a new patient-controlled medical therapeutic device or the system may be added to an already existing device. Other features and advantages of the example embodiments are described.

38 Claims, 5 Drawing Sheets

OTHER PUBLICATIONS

"Biometric Glossary of Terms," BiometricsDirect.com™. Retrieved from the Internet: <URL: http://www.biometricsdirect.com/Content/Biometric_Terms.htm>, retrieved Mar. 22, 2005.

"FAQ," BiometricsDirect.com™. Retrieved from the Internet: <URL: http://www.biometricsdirect.com/Content/FAQ.htm>, retrieved Mar. 22, 2005.

"Fingerprint Biometrics—Block Diagram," Texas Instruments. Retrieved from the Internet: <URL: http://focus.ti.com/vf/docs/blockdiagram.tsp?familly=vf&blockDiagramId=6020, retrieved Mar. 22, 2005.

"Fingerprint Biometrics," Identix® Retrieved from the Internet: <URL: http://www.identix.com/trends/finger.html>, retrieved Mar. 22, 2005.

"HIPAA/JCAHO Compliance," BiometricsDirect.com™. Retrieved from the Internet: <URL: http://www.biometricsdirect.com/Content/HIPAA.htm>, retrieved Mar. 22, 2005.

"LifeCare PCA® 3 Infusion System," Hospira. Retrieved from the Internet: <URL: http://www.hospira.com/Products/LifeCarePCA3InfusionSystem.aspx >, retrieved Mar. 22, 2005.

"Patient controlled analgesia by proxy," Sentinel Event Alert, Issue 33—Dec. 20, 2004 Print Version. Retrieved from the Internet: <URL: http://www.jcaho.org/about+us/news+letters/sentinel+event+alert/print/sea_33.htm>.

"PCA Pumps," Hospira. Retrieved from the Internet: <URL: http://www.hospira.com/Products/PCAPumps.aspx>, retrieved Mar. 22, 2005.

"Priming Sets Loading PCA Vials," Hospira, Lifecare® PCA 3 Infusion System, <URL:http://www.hospira.com>, retrieved Mar. 22, 2005.

"Products Overview," BMF Biometrics Fingerprint Sensor. Retrieved from the Internet: <URL: http://www.bm-f.com/products/overview.html>, retrieved Mar. 22, 2005.

"Project Listing—Patient Controlled Analgesics," Cognitive Engineering Laboratory. Retrieved from the Internet: <URL: http://www.mie.utoronto.ca/labs/cel/research/sponsor/pca.htm>, retrieved Mar. 22, 2005.

"Safer Patient-Controlled Analgesia: A Clinical Perspective," Hospira 2004.

G., Juhl, "[The Infucommand. A PCA (patient-controlled analgesia) device using pulsoximetric bolus control]" Anaesthesist. Apr. 1990;39(4):236-9, PubMed Abstract. Retrieved from the Internet: <URL: http://www.ncbi.nlm.nih.gov/entrez/query.fcgi?cmd=Retrieve&db=PubMed&list_uids=23...>.

Hicks, et al., "USP Drug Safety Review: Errors involving PCA pumps," Oct. 25, 2004. Retrieved from the Internet: <URL: http://www.drugtopics.com/drugtopics/content/printContent/Popup.jsp?id=129117>.

Marders, Julia, "PCA by proxy: Too much of a good thing," Nursing 2004, vol. 34, No. 4. Retrieved from the Internet: <URL: http://216.239.57.104/search?q=cache:65UM8YOLoqIJ:www.fda.gov/cdrh/psn/article-dev...>.

Murhammer, et al., "Patient-Controlled Analgesia: Review of Safety Issues," Rx Update: Aug. 2003. Retrieved from the Internet: <URL: http://www.vh.org/adult/provider/pharmacyservices/RXUpdate/2003/08rxu.html>.

Rapp, et al., "Patient-controlled analgesia: a review of effectiveness of therapy and an evaluation of currently available devices," DICP, The Annals of Pharmacotherapy: vol. 23, No. 11, pp. 899-904. Retrieved from the Internet: <URL: http://www.theannals.com/cgi/content/abastract/23/11/899>, retrieved Mar. 22, 2005.

\* cited by examiner

METHOD AND APPARATUS FOR PATIENT-CONTROLLED MEDICAL THERAPEUTICS

FIELD OF INVENTION

The present invention relates to methods and apparatuses for use in medical therapeutics, and more specifically, relates to methods and apparatuses in which the patient can control the dispensing of medical therapeutics, such as pain medication, anesthesia or other medication or therapies.

BACKGROUND

Pain management remains an area of heightened concern for the health care industry. The most prevalent and traditional method of pain management is nurse-administered analgesia. Analgesic describes a medication that alleviates pain. Nurse-administered analgesia typically results in larger and less frequent doses of pain medication than more modern methods. This form of dosing can lead not only to less efficacious pain control but also significant complications like over-sedation, respiratory depression and death.

More recently, patient-controlled analgesia ("PCA") and patient-controlled epidural analgesia ("PCEA") have become the preferred methods of administering analgesic as they allow the patient to uniquely control his or her own pain. These devices and similarly operative devices, in which a patient manages his or her pain, are collectively referred to herein as "PCA" devices. In comparison with the nurse-administered analgesic method, the PCA is designed to allow delivery of a smaller amount of analgesic in a more frequent dosing pattern. Typically, a PCA device is set up next to the patient and is programmed by a nurse or authorized caregiver to deliver certain analgesics to the patient upon the patient's command or request. To receive the command, there is typically a cable or wire attached to the device with a button on the end that extends to the patient. The patient can press the button to give a prescribed amount of intravenous or epidural analgesic to him or herself.

It is thought by some in the health care industry that patients can develop a synergism with the PCA device and can effectively manage their pain with less medication thus decreasing side effects like pruritus, dysphoria, hypotension, hypoventilation, bradycardia, and nausea/vomiting. In addition, the PCA device prevents overmedication, and therefore, significantly reduces the risk of cardiopulmonary compromise (e.g., respiratory depression) and death. In the advancement of pain management, then, many PCA type devices have been released on the market and have become a popular form of pain management. Early models usually consisted of a syringe pump connected to a timing mechanism used as a safeguard to prevent an overdose. At the push of the button by the patient, pain medication is administered in small bolus doses assuming a minimum amount of time between each dose has expired. More modern PCA devices include microprocessors to digitally manage lockout intervals and dosage amounts, yet such devices still operate with a simple push button command.

Even with the advancement of modern PCA devices, some patients are still receiving too much analgesic, therefore leading to life-threatening complications. While it is typically believed that a sedated patient will not press the button to deliver more medication, family members, caregivers, and sometimes clinicians are administering the analgesic for the patient by "proxy," (also referred to herein as "PCA by proxy") hoping to keep the patient comfortable. This well-intentioned effort has been reported to lead to major complications, up to and including death. Indeed, the Joint Commission on Accreditation of Healthcare Organization ("JCAHO") has recognized the importance and danger of PCA by proxy and issued a sentinel event alert concerning the issue on Dec. 20, 2004.

One current approach to addressing PCA by proxy is to educate the healthcare industry, patients, families, and visitors to the hazards of improper PCA use. Another approach is provided in U.S. Pat. No. 6,899,695, entitled "Medication Security Apparatus and Method," given to Herrera, which uses a voice sound recognition algorithm to create a voice print that distinguishes the patient's voice command from other voices to ensure that only the patient controls the bolus dose to himself or herself.

There continues to be a need for improved pain management. Unlike the traditional nurse-administered methods of pain management, with PCA devices, the patient provides a measure of safety him or herself because an over-sedated patient will not be capable of pushing the PCA button. Thus, the previous doses can "wear off" by the processes of redistribution and elimination effectively moving the patient towards safety rather than overdose and complication. PCA by proxy has been identified as a significant breakdown of this effective and otherwise safe device. A need still exists to significantly reduce or eliminate the risk of PCA by proxy in a way that provides a seamless transition from current methods and can be used effectively in a hospital or other patient care setting.

BRIEF DESCRIPTION OF THE DRAWINGS

Many aspects of the example embodiments may be better understood with reference to the following drawings. The components in the drawings are not necessarily to scale, emphasis instead being placed upon illustrating example embodiments.

DETAILED DESCRIPTION

I. Overview

Figure 1:
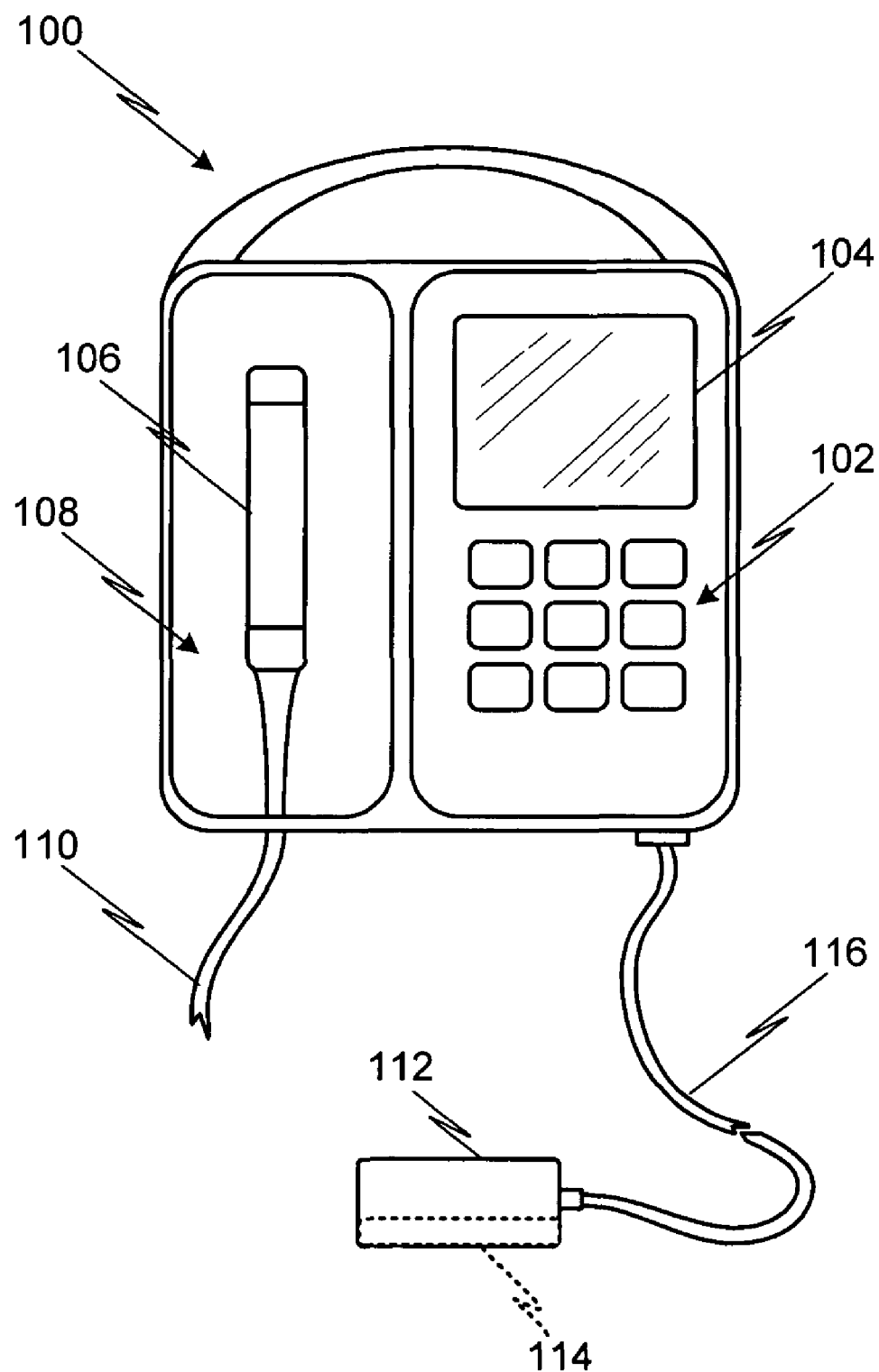
FIG. 1 illustrates a front-view of an example patient-controlled device for use in administering medication to a patient upon command from that verified patient.

An apparatus and associated methods are provided for use in patient controlled medical therapeutics and the use of biometric technology to authenticate patients. The preferred embodiments are directed towards apparatus and associated methods for use in patient controlled pain management and the delivery of analgesic, but the invention is not limited to pain management and could be applied to any medical therapeutic generally, including anesthesia, other medications and therapies. The preferred embodiments are also directed towards the use of fingerprint biometrics to authenticate patients, but the invention is not so limited and could be applied to any biometric technology that is suitable for use in a hospital environment.

The apparatus of the preferred embodiments includes the use of a pushbutton and a fingerprint sensor to authenticate the patient before a prescribed dose of medication is administered to the patient. In response to an activation, the fingerprint sensor captures an image of the patient's finger and relays the information to a processor, which determines whether a match exists with a previously stored fingerprint. Activation of the fingerprint sensor is preferably caused by the depression of a pushbutton. If the patient depresses the pushbutton outside of a lockout period (if any such lockout period or time limit is programmed) and the fingerprint match is successful, the processor will send a signal to a release mechanism/delivery device (a pump in a preferred embodiment) corresponding to the PCA device to subsequently release medication (e.g., analgesic) from a vial or container to the patient. While the use of a pushbutton is not required, example embodiments described herein include the use of a button or pushbutton to indicate the patient's intention of requesting more pain medication; "pushbutton," as used herein, refers to any type of actuation device and includes any type of pressure sensitive surface, switch, or button. Any such actuation device may be substituted herein for "pushbutton." With respect to other biometric technologies, such as retinal scanners, other actuation devices as known in the art could be used.

In an alternative example embodiment, upon a successful fingerprint depression of the pushbutton and match, the PCA device may initiate some other form of pain management that does not necessarily include liquid medication. Examples of other forms of pain management include iontophoresis, which involves ion movement through biological tissue under the influence of an electric current, and transdermal, in which a drug is introduced into the body through the skin.

The example embodiments overcome drawbacks typically found in modern PCA type devices by authenticating the patient using fingerprint biometric technology before analgesic is released. This authentication process will reduce or eliminate the risk of "PCA by proxy" and its attendant complications. The use of a fingerprint scan effectively prevents the unauthorized use of the PCA device because it requires authentication of the patient in a way that cannot be easily copied or recorded like other authentication means.

The example embodiments are also effective and suitable for use in a hospital or other patient care facility, in which the preferred atmosphere is one of a quiet and peaceful nature. By using fingerprint biometric technology, the amount of added "noise pollution" to the environment is kept to a minimum. This remains true even if the patient requests hundreds of doses of analgesic in a twenty-four hour period. This feature is especially important when patients share rooms or when family or friends are gathered in the patient's room.

According to one example embodiment, the security device is packaged in a manner that makes a near seamless transitional device change from the conventional pushbutton method. Integrating fingerprint biometric technology with that of a pushbutton makes for a smooth and relatively easy transition from a non-secure method of pain management to one that is secure.

According to another example embodiment, the security device includes an encasement or housing to prevent unauthorized dispensing of analgesic. In this embodiment, the encasement makes it increasingly difficult to use the patient's finger (or a false finger) to dispense analgesic without the patient's need or consent.

The example embodiments can be utilized with existing PCA devices or completely integrated with new PCA devices. To use with existing PCA devices, for example, the fingerprint authorization process can be integrated with the traditional pushbutton mechanism. The traditional pushbutton may be left attached and the fingerprint authorization mechanism may be added to the system, such that a command to dispense analgesic comes only after the pushbutton is depressed and authorization occurs. Alternatively, the traditional pushbutton may be removed and replaced by an integrated pushbutton and fingerprint sensor. Of course, the example embodiments may also be completely integrated into the design of new PCA devices. It will be understood that the system can be programmed such that the example steps described herein (e.g., depressing the pushbutton and scanning the fingerprint) can occur in any order or at the same time. Also, it will be understood that "depressing the pushbutton," as used herein, can include the steps of depressing the pushbutton and releasing, or can include only depressing the pushbutton (not requiring the step of releasing).

Additionally, while the fingerprint authorization mechanism may be used to authenticate the patient when administering doses, the authentication mechanism can also be used to authenticate other users of the PCA device, such as physicians and caregivers, before giving them access to program the PCA device or provide an extra, but necessary dose to the patient. This feature may be especially useful for pediatric patients when parents (or other persons) are authorized to use the PCA device on behalf of the child. Alternatively, a separate fingerprint sensor may be used to authenticate other users of the PCA device.

Other features and advantages of the apparatus and associated methods will become apparent to one with ordinary skill in the art upon examination of the following drawings and description. Additionally, the teachings described herein, such as a security device for a PCA device using a fingerprint authenticating mechanism, may be applied to other types of medical devices that are used to dispense medication or other forms of therapy to a patient. As such, the present invention is not to be limited to the example embodiments described herein, and particularly, the present invention is not to be limited to use with any particular type of patient-controlled analgesia device.

II. Example Pain Management Apparatus and Associated Methods

FIG. 1 illustrates an example PCA-type apparatus 100 with a fingerprint sensor/pushbutton 114 for use in administering controlled doses of medication (e.g., analgesic) to an authenticated patient. The example apparatus 100 generally includes, but is not limited to, a video display 104, function keys 102 for programming the apparatus 100, a container (such as a drug vial) 106 for storing medication or analgesic, a delivery device or release mechanism (e.g., a pump) 108 for releasing medication or analgesic, tubing 110 for delivering the medication to the patient intravenously or through some other method of delivery, actuation device 112 which includes a fingerprint sensor/pushbutton 114 and corresponding conductive wire 116 for providing the authentication signal (the request for medication) to the delivery device/release mechanism of the apparatus 100.

The present invention is not limited to any particular type of container for storing medication or to any particular type of delivery device/release mechanism. For example, the present invention can utilize iontophoresis combined with a transdermal patch in which medication is delivered through a transdermal patch and in which the delivery is controlled electronically.

According to the example embodiments, the apparatus 100 is generally placed next to the patient's bed and the actuation device 112 may be held remotely by the patient or clipped to the bed near the patient. The apparatus 100 may also be carried by a handle or wheeled if the device has been fastened to a wheeled pole. Power may be provided to the apparatus 100 by a wall outlet or through some other power source like batteries (not shown in the figure). Power converters (also not shown in the figure) may be used to adjust the voltage to levels required to operate the control module, release mechanism/delivery device, and/or other electronics corresponding to the apparatus 100.

To program the apparatus 100, it may be desirable to first require a password or some other means of authentication. For instance, the physician or authorized caregiver may enter their password to gain access to the control unit of the apparatus 100. Alternatively, the control unit of the apparatus 100 may be programmed to read the physician or authorized caregiver's fingerprint through fingerprint sensor/pushbutton 114. In another alternative embodiment, the physician or caregiver may have their fingerprint scanned by another machine for authentication (e.g., not fingerprint sensor/pushbutton 114), in which case, the control unit of the apparatus 100 is in direct or indirect communication with the other machine to receive the fingerprint or an authorization signal. Just like the patient, to be described below, the physician or caregiver can have their fingerprint initially scanned by any designated fingerprint sensor (which can be the same as or different from fingerprint sensor/pushbutton 114) and stored at the apparatus 100, or alternatively, in a database reachable by an accessible network. Regardless of how the fingerprint is scanned, if the fingerprint of the physician or caregiver matches a pre-recorded fingerprint stored into memory of the control unit or stored remotely in a database accessible over a network, then access may be granted.

A physician or authorized caregiver may program the apparatus 100 through function keys 102 and video display 104 to deliver—when commanded by the patient—certain sized doses of medication to the patient at limited intervals. These time limits are also referred to herein as "lockout periods," such that the medication will not be administered at any time during or within a lockout period. These lockout periods can be programmed for any reason, but are particularly useful to prevent the patient from receiving too much medication. The apparatus 100 may also be programmed to continuously dispense medication to the patient as indicated. Moreover, the type of medication contained in the container 106 may also be programmed into the control unit of the apparatus 100 through keys 102 and display 104. In another embodiment and generally found in more sophisticated and modern PCA devices, the container 106 may contain a bar code that, if provided, a bar code reader on apparatus 100 can read the vial's bar code to automatically program some pertinent information, thereby reducing the chance for operator error. Other types of systems may exist or will be developed in the future that can be used to prevent this type of operator error. Dosing quantities and lockout periods, such as specific time interval limitations, may also be programmed into the control unit automatically via a bar code on the container 106 or through some other mechanism.

When in operation, the patient can control, preferably within the programmed limits, the amount of medication that is dispensed by placing a finger (whichever fingerprint(s) was previously stored into memory of the control unit or stored remotely in a database accessible over a network) over the pushbutton and fingerprint sensor 114 of the actuation device 112 for authentication. According to one example embodiment, to request a dosage of medication the patient depresses a button in the actuation device. The pushbutton may be integrated with the fingerprint sensor 114, such that upon depression of the pushbutton, the fingerprint sensor 114 will scan the fingerprint. It is understood that while the pushbutton and the fingerprint sensor 114 may be integrated, the preferred function of the fingerprint sensor 114 is to determine whether the patient is authenticated and the preferred function of the button is to determine the patient's intentions (e.g., determining whether the patient is simply resting his/her finger on the actuation device or whether the patient is requesting more pain medication). As previously stated above, other types of actuation devices may be used in place of the pushbutton. Also, if a pushbutton is used, it does not have to be integrated with the fingerprint sensor. It should also be understood that while the example embodiment calls for scanning the fingerprint upon depression of the button, the present system is not to be limited; for example, the fingerprint sensor may periodically and continuously scan the finger resting on the button such that upon depression of the button, the patient has already been verified.

Once the patient is authenticated and the button is depressed, and if the requested dose is within the programmed limits, the delivery device/release mechanism 108 (in one preferred embodiment, a pump) will automatically dispense a controlled amount of medication from the container 106 to the patient through tubing 110. If liquid medication is not used, then instead of dispensing analgesic in liquid form to the patient, another form of pain management or treatment can be initiated upon authentication and button depression (e.g., iontophoresis, etc.) If the patient cannot be verified through the fingerprint sensor/pushbutton 114 or an unauthorized person has attempted to deliver a dose of medicine, then in addition to not providing a dose of medicine, the control unit may provide an alert, which can be an audible or visual alert, electronic message or any other type of alert. The alert may remain local to the apparatus 100, and if so desired, an alert signal may be automatically transmitted to a nurse's station or desk to notify a caregiver that the patient cannot be authenticated or of an error that requires attention.

The history of all button presses, fingerprint scans, and alerts, among other things, may be stored either at the apparatus 100 or in a database on a network. This data may be useful to determine information like the number of button presses, when the button presses occurred, who attempted to press the button, the type of dosage given, the amount of medicine given and so on. This information can be useful for security reasons as well as for treatment of the patient.

According to one example embodiment, the actuation device 112, which includes the fingerprint sensor 114, is not covered or encased. Rather, the fingerprint sensor 114 and button are exposed so that a patient can easily and effectively command a dose of analgesic. In this embodiment, the actuation device 112 provides a seamless transition from current methods (e.g., the use of a button to dispense medication), yet the present system provides an effective means to authenticate the patient before dispensing pain medication. This example embodiment may be useful for any application, but particularly useful for users with rheumatoid arthritis (who require simple maneuvering), those with language barriers, variable IQ levels, and so on by providing a straightforward pain management solution.

It is envisioned that in some instances, however, a person other than the patient may attempt to override the authentication process by placing the patient's finger on the pushbutton/ fingerprint sensor and pressing the button, thereby dispensing an extra and perhaps unneeded dose of analgesic to the patient. This may happen during times when the patient is sleeping, unconscious, or without consent of the patient. In view of this, the actuation device 112 may include a covered or encased sensor to prevent someone from wrongfully using the patient's finger (or a false finger) thereby providing an unauthorized dose of medication to the patient.

Figure 2:
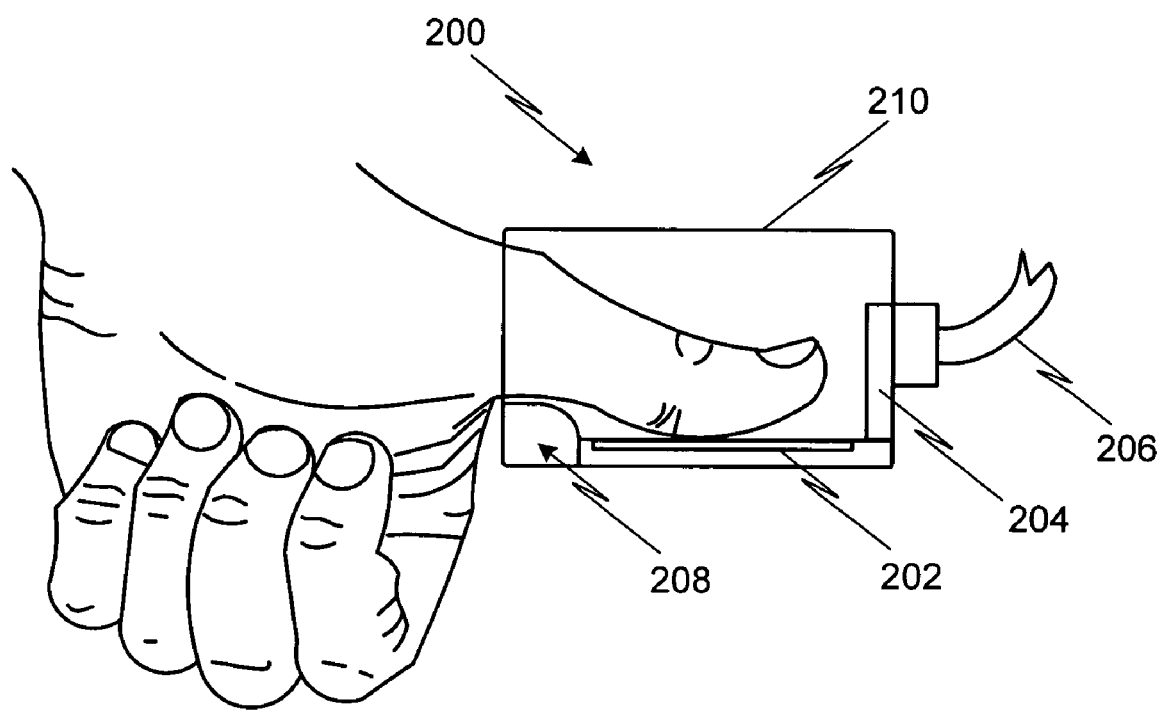
FIG. 2 illustrates a cutaway side-view of an example fingerprint sensor for use with the patient-controlled device shown in FIG. 1, the example fingerprint sensor is used for patient fingerprint sampling and authentication.

An example of this alternative embodiment is shown in FIG. 2. More specifically, FIG. 2 illustrates an example of an encased actuation device 200, which was previously shown in FIG. 1 as 112, for use in authenticating a patient. Actuation device 200 includes a housing or encasement 210 for encasing fingerprint sensor/pushbutton 202, authentication electronics 204, and stop 208. The housing or encasement 210 may be connected to the fingerprint sensor/pushbutton 202 in any manner. This housing 210 may be made of rigid plastic or an equivalent material. According to this example, the patient inserts a finger into the opening of the fingerprint sensor 200 and upon depression of the button (or simply applying pressure to the button or surface); the fingerprint sensor/button 202 captures an image of the finger. The pushbutton is used in combination with the fingerprint sensor 202 to initiate the authentication process. Preferably, the encasement design is such that flexion at the distal interphalangeal joint ("DIP") would be necessary, more of which is described below.

Irrespective of whether the pushbutton and fingerprint sensor are encased or not, the process of scanning and authentication preferably remains the same. Fingerprint scanning is generally the acquisition and recognition of a person's fingerprint characteristics for verification purposes. This allows the recognition of the patient through quantifiable characteristics that verify the patient's identity. Any types of finger-scanning technology may be utilized. Example methods include an optical method, which starts with a visual image of a finger, and another method that uses a semiconductor-generated electric field to image a finger. It is to be understood that the present system is not limited by the finger-scanning technology utilized.

Fingerprint sensor/pushbutton 202 then communicates data corresponding to the image or some form thereof to the authentication electronics 204. Authentication electronics 204 generally includes memory and a digital signal processor for executing stored program instructions that determines whether a match has occurred with a fingerprint stored into memory and the image. Authentication electronics could embody actual circuitry or be software that works in conjunction with a processor. Examples of fingerprint matching techniques may include minutiae-based and/or correlation based techniques. If a match is found, a signal from the authentication electronics 204 travels to the release mechanism/delivery device and/or control unit of the apparatus through wire 206 to dispense the medication. The authentication electronics 204 may be positioned as shown near the fingerprint sensor/ button or anywhere, such as at the PCA device itself or remotely and accessible via a network or some other means.

In an effort to reduce or eliminate the possibility of overriding the authentication process, a stop 208 may be utilized so that the patient has to bend his or her finger inside the actuation device 200 to activate the authentication process. Of course, the actuation device 200 may be designed differently to produce the same or similar results, such as an angled surface, which would require articulation at the DIP joint. For example, the actuation device 200 could be designed such that the patient has to insert his or her entire finger or a substantial portion of the finger into the device—thereby making it increasingly difficult for someone other than the patient to activate the authentication process.

If an encased design is utilized, it is preferable to have a "one-size fits all" device for ease and convenience. However, it is also envisioned that various sizes may be used to accommodate differing finger sizes. Additionally, it is preferred that the encasement can be removed for easy cleaning. As an additional safeguard, the actuation device 200 may include a sensor that sends a signal to the PCA device when the encasement is removed and the fingerprint sensor/pushbutton are exposed. This signal could cause the PCA device to decline from providing a dose of medication if requested. Alternatively, or in addition to a removable encasement, a thin film may be inserted over the patient's finger or placed directly into the encasement and over the fingerprint sensor/pushbutton for each user. For sanitary purposes, the thin film can be thrown out and replaced for each user. Alternatively, the actuation device 200 or any part thereof may be disposable such that it could be allocated to a single user or a limited number of users.

It is to be understood that the present invention is not limited to the actual design and/or layout shown in FIG. 1 or FIG. 2. It will be appreciated by those of ordinary skill in the art that other designs and/or layouts may be utilized to provide a security mechanism for authenticating a patient by his or her fingerprint before a dose of pain medication is administered. For example, in an alternative embodiment to the actuation device 200 shown in FIG. 2, some or all of the authentication electronics 204 may be moved to a location at the apparatus 100 or to some other location accessible through a network. In such an alternative, the data from the captured image at the fingerprint sensor 202 may be communicated over a wire (or wirelessly) to the authentication electronics at the apparatus where it is determined whether a match exists. The flexibility of the design and/or layout is further described with respect to FIG. 3.

Figure 3:
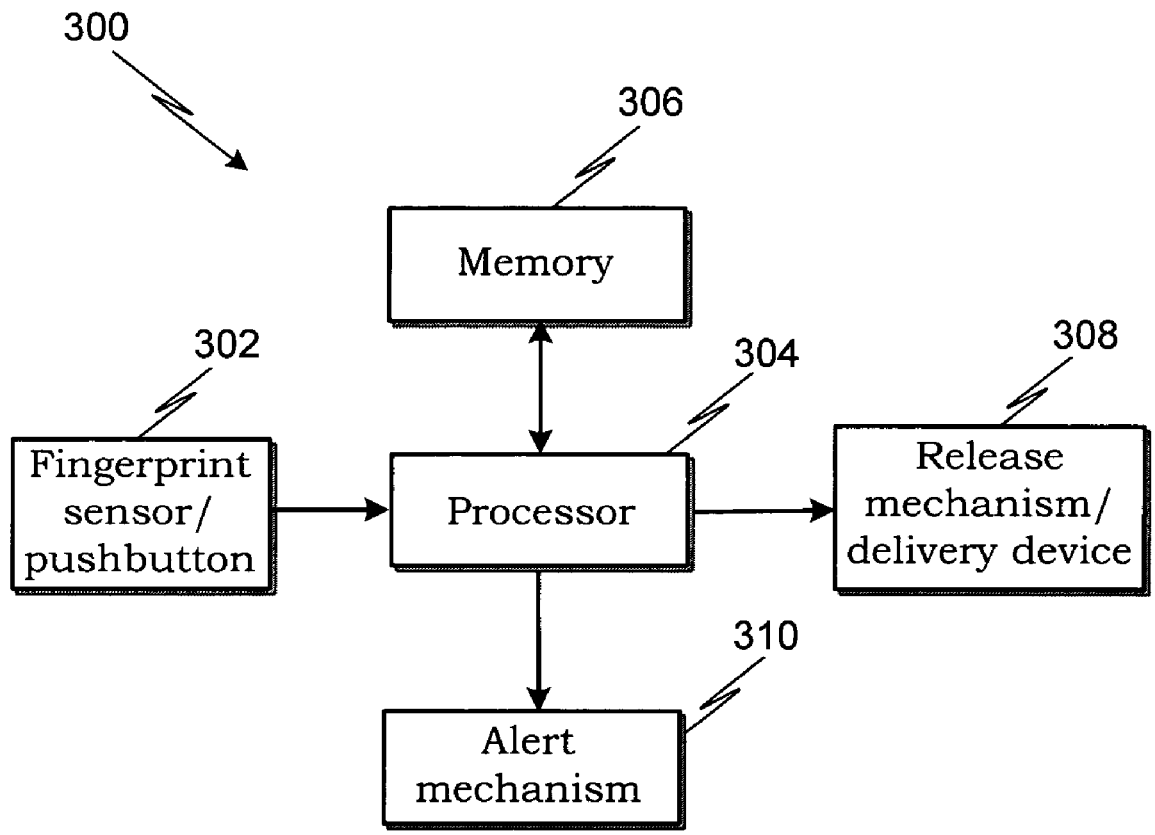
FIG. 3 illustrates a block diagram of the various components that may be used by the example patient-controlled device shown in FIG. 1 to authenticate the patient and release the medication.

FIG. 3 illustrates a block diagram 300 of various components that may be used to administer medication to an authenticated patient. Included in the diagram 300 are fingerprint sensor/pushbutton 302, processor 304, memory 306, release mechanism/delivery device (e.g., a pump) 308, and alert mechanism 310. Each of the components may communicate with each other through a wired or wireless connection, and therefore, the actual placement of the components may be of little significance (e.g., FIG. 2 provides an example placement).

An example of a commercially available fingerprint sensor is BLP-100, which is a pressure sensitive fingerprint sensor manufactured by BMF Corporation, in Japan. In a preferred embodiment, a pushbutton is integrated with the fingerprint sensor. Once the pushbutton is depressed, the fingerprint sensor can scan the patient's fingerprint.

An example processor is BCT-100, which is a controller for the BLP-100 and also manufactured by BMF Corp. Alternative examples include the Fingerprint Biometric System from Texas Instruments. Some aspects of the authentication process may be embodied in the form of a computer program product that is stored on a computer readable storage medium and is executed by a suitable instruction system. Any suitable computer readable medium may be utilized including hard disks, CD-ROMS, optical storage devices, magnetic storage devices, or any type of known computer readable medium.

Memory 306 includes permanent and/or temporary memory such as read only memory ("ROM"), random access memory ("RAM") or any variation of RAM, such as static RAM or static-dynamic RAM. The memory 306 may be on board the PCA device or additionally on a network that is readily accessible by the PCA device. According to a network accessible embodiment, the diagram 300 may show the various components communicating with a network such that the fingerprint samples may be stored and/or downloaded from a database accessible over the network. A central depository of authorized fingerprint(s) may then be kept at the hospital or facility. Also, if so desired, limitations and/or rules can be programmed into the database to allow only certain users to be authorized for particular PCA device(s) (e.g., a particular nurse may be authorized for PCA device #2, #3, and #4, but not for #5 or #1). This embodiment will preferably limit the number of times a physician or caregiver will have to input their fingerprints.

In a preferred embodiment, release mechanism/delivery device 308 is an infusion-type pump that infuses fluids, medication or nutrients into a patient's circulatory system upon verification of the patient. For example, it may be used intravenously, although subcutaneous, epidural, intrathecal infusions, or others systems/methods may also be used.

The alert mechanism 310 may include a speaker for making certain programmed noises when such alert is needed. The alert mechanism 310 may be triggered during the fingerprint scanning process, when the dose is administered, or when the user cannot be authenticated. The alert mechanism 310 may exist on the PCA device itself or at some other location on a network. The alert mechanism 310 may also include logging the alerts in a database, either on the PCA device itself or in a database on the network. Further, the speaker may be used to provide auditory cues while using the device. For example, differential sounds may be used to indicate an accepted versus rejected fingerprint scan and authentication.

Figure 4:
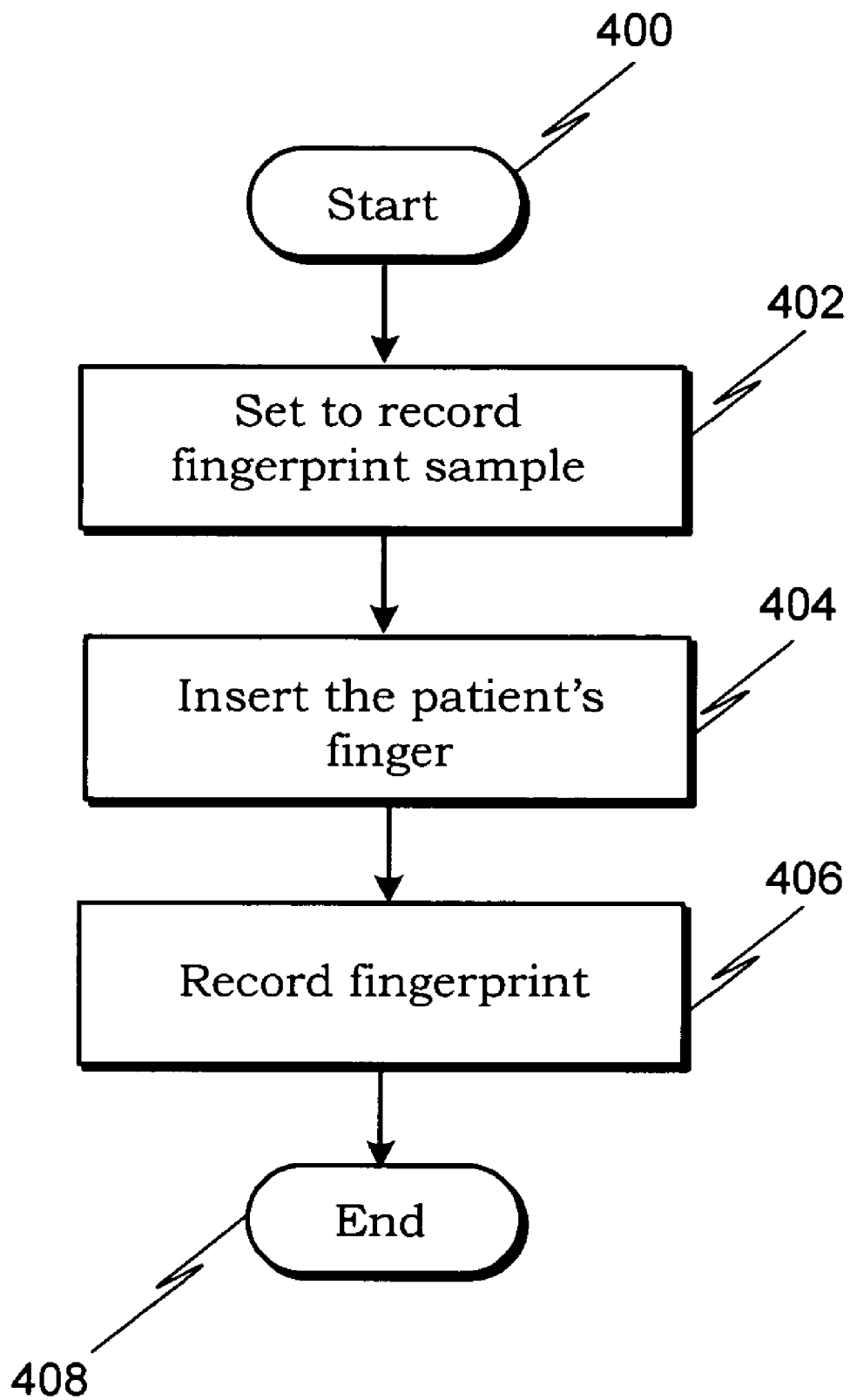
FIG. 4 shows a flow chart for illustrating an example process of recording a patient's fingerprint for use in later authenticating the patient.

FIG. 4 shows a flow chart illustrating an example process of recording a patient's fingerprint for use in authentication. Various blocks in FIG. 4 may represent a module, segment, or portion of code, which includes one or more executable instructions for implementing specific logical functions or steps in the process. Alternate implementations are included within the scope of the preferred embodiments in which functions may be executed out of order from that shown or discussed, including substantially concurrently or in reverse order, depending on the functionality involved, as would be understood by those reasonably skilled in the art. Further, it is understood that some steps may not need to be actually implemented to achieve the desired result of scanning the patient's fingerprint into memory.

At block 400, the apparatus 100 is turned "on" and is ready to accept input commands from the operator (e.g., a physician, caregiver, or some other authorized user). Power is also supplied to the fingerprint sensor/pushbutton 114. According to one example embodiment, the fingerprint sample is taken at the PCA device. According to an alternative, the fingerprint sample is taken on another machine using a different fingerprint sensor and is stored in a database that is accessible by the PCA device over a network or accessible by some other mechanism.

At block 402, the authentication module is set to record a fingerprint sample. In this state, the module is ready to receive a new fingerprint. Previous fingerprint samples may be discarded or the new fingerprint may be added to the system. Preferably, an alert is provided to indicate that the module is ready for the patient to insert his or her finger.

At block 404, the patient inserts his or her finger into the actuation device and presses the finger against the pushbutton. In addition to encased designs, as previously mentioned, to prevent false fingers from being used the system may also incorporate a device to measure blood flow or check for correctly arrayed ridges at the edges of the fingers.

At block 406, the fingerprint sensor scans the patient's fingerprint and records its characteristics. Various characteristics of the fingerprint, such as whorls, arches, and loops may be recorded along with the patterns of ridges, furrows, and minutiae—the type of information and the amount of information recorded may depend on the scanning technology or algorithm used. This information may then be processed or stored into memory as an image or as an encoded computer algorithm to be compared with other fingerprint samples. According to another embodiment, the fingerprint samples can be stored anywhere, such as in memory on the network. An alert may be provided to indicate the fingerprint scan was successful. If the scan was not successful, then a different alert may indicate to try the process again. Further, additional fingerprint scans can take place (e.g., to record a caregiver's fingerprint for his or her authentication, and so on).

At block 408, the process of recording a fingerprint sample ends.

Figure 5:
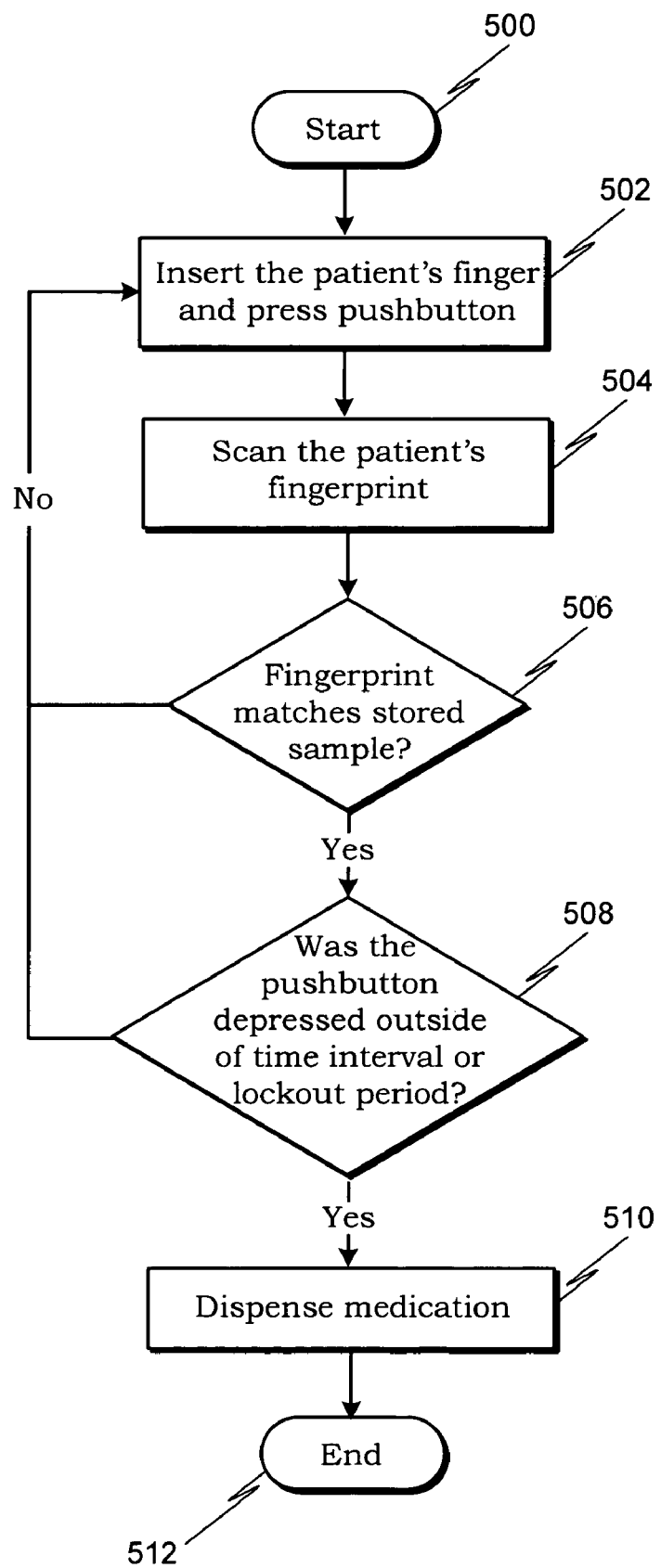
FIG. 5 shows a flow chart for illustrating an example process for authenticating a patient for delivery of medication by comparing a scanned fingerprint to a previously stored fingerprint.

FIG. 5 shows a flow chart for illustrating an example process for authenticating a patient for delivery of medication by comparing a scanned fingerprint to a recorded one. Various blocks in FIG. 5 may represent a module, segment, or portion of code, which includes one or more executable instructions for implementing specific logical functions or steps in the process. Alternate implementations are included within the scope of the preferred embodiments in which functions may be executed out of order from that shown or discussed, including substantially concurrently or in reverse order, depending on the functionality involved, as would be understood by those reasonable skilled in the art. Further, it is understood that some steps may not need to be actually implemented to achieve the desired result.

At block 500, the control module and the authentication module are powered and ready to receive a command from the patient.

At block 502, the patient places his or her finger over the pushbutton and fingerprint sensor. As described earlier, in one example embodiment, the pushbutton and fingerprint sensor are not encased, so the patient can simply place the finger over the pushbutton. Also described earlier, in another example embodiment, the pushbutton and fingerprint sensor are encased, so the patient will insert his or her finger into the housing and place it on the pushbutton.

At block 504, the patient or authorized caregiver depresses the pushbutton and the fingerprint sensor scans at least a portion of the patient's fingerprint. As described earlier, the system is not limited to any particular order of operation. For instance, the system may be programmed to receive a signal from the pushbutton first, and then the fingerprint sensor will scan the fingerprint. In another instance, the system may be programmed to periodically scan the fingerprint and then the patient can depress the pushbutton at any time. In yet another instance, the pushbutton and fingerprint sensor may perform their function at the same time. Regardless of operation, the system preferably recognizes that the patient is requesting another dose of medicine (e.g., through the activation of the pushbutton) and the system is attempting to authorize the patient (e.g., through the scanning of the fingerprint).

At block 506, the software then searches for similar information in the database (in memory at the PCA device or on a network). Often an algorithm is used to encode the information into a character string that can be searched for in the database, improving search time. The database may not actually have an image of the fingerprint, but a set of data representing the fingerprint that can be used for comparison. If the fingerprint does not match, the patient is denied and the process can go back to block 502. If the fingerprint does match (authentication), then the process goes to block 508.

At block 508, it is determined whether the pushbutton was depressed outside of a programmed time limit or lockout period. If the pushbutton was depressed within such a programmed time limit or lockout period, the patient is denied and the process can go back to block 502, If the pushbutton was depressed outside of the programmed time limit or lockout period, the process goes to block 510 for delivery of medication.

At block 510, a prescribed dose of medication is dispensed by the release mechanism/delivery device to the patient. The process can again be repeated at block 500.

At block 512, the example process for authenticating a patient for delivery of medication ends.

As previously mentioned, the history of all button presses and/or fingerprint scans may be stored—either at the PCA device or on the network. It may be useful to know who was pressing the button and when the button was pressed and/or if the patient was authenticated. It may also be useful to record information related to the authentication such as medication type, dosage, frequency, programmed amounts, and so on. A paper report or an electronic report, or both can be generated with this type of information.

III. Conclusion

The example embodiments described herein provide for an improved device for dispensing medication (in a preferred embodiment, analgesic) to a patient using a fingerprint analyzer. The example embodiments are described in relation to a patient-controlled analgesia device that delivers a prescribed amount of intravenous or epidural analgesic to the patient when he or she activates the release mechanism/delivery device and upon fingerprint verification. Of course, the teachings described herein may be applied to other patient controlled medication dispensing devices or patient controlled therapy. The teachings described herein may also be applied to other types of biometric technology that would be suitable for use in a hospital environment.

An advantage of the apparatus and associated methods includes the prevention of someone other than the patient from activating the release mechanism/delivery device. This eliminates or reduces the risk of administering the analgesia for the patient "by proxy." Thus, the present system eliminates or reduces this potentially dangerous aspect of modern PCA devices.

Another advantage is that the fingerprint authentication mechanism may be used with existing PCA type devices to prevent unauthorized use of the device. It provides a seamless transition from current methods to one that provides an effective means by which the patient or user is authorized.

Another advantage of the apparatus and associated methods is that it can be operated in the peaceful and quiet surroundings normally associated with a hospital or patient care facility, e.g., nursing home or some other environment where a patient would require use of a PCA device.

Another advantage is that the fingerprint samples may be stored at the PCA device or in a database accessible over a network. According to the network embodiment, a central database may be utilized to store fingerprints for use in authenticating the user. In this way, a physician or caregiver can be authorized for any PCA device within communication of the network. Also, if so desired, limitations and/or rules can be programmed into the database to allow only certain users to be authorized for particular PCA device(s).

The example embodiments of the present invention have been described herein. It is to be understood, of course, that changes and modifications may be made in the example embodiments without departing from the true scope of the present invention. Aspects of the example embodiments may include logic to implement the described methods in software modules as a set of computer executable software instructions. A processor implements the logic that controls the operation of the authentication mechanism. The processor executes software that can be programmed by those of skill in the art to provide the described functionality.

The software can be represented as a sequence of binary bits maintained on a computer readable medium described above, for example, as memory device 306 in FIG. 3. The computer readable medium may include magnetic disks, optical disks, and any other volatile or (e.g., Random Access memory ("RAM")) non-volatile firmware (e.g., Read Only Memory ("ROM")) storage system readable by the processor. The memory locations where data bits are maintained also include physical locations that have particular electrical, magnetic, optical, or organic properties corresponding to the stored data bits. The software instructions are executed as data bits by the processor with a memory system causing a transformation of the electrical signal representation, and the maintenance of data bits at memory locations in the memory system to thereby reconfigure or otherwise alter the unit's operation. The executable software code may implement, for example, the methods as described above.

It should be understood that the programs, processes, methods and apparatus described herein are not related or limited to any particular type of vial or container, pumps, processors, memory or storage devices, display units, input capabilities, and so on, unless indicated otherwise. Various types of general purpose or specialized processors may be used with or perform operations in accordance with the teachings described herein.

It should further be understood that a hardware embodiment might take a variety of different forms. The hardware may be implemented as an integrated circuit with custom gate arrays or an application specific integrated circuit ("ASIC"). The embodiment may also be implemented with discrete hardware components and circuitry. In particular, it is understood that the logic structures and method steps described in the flow diagrams may be implemented in dedicated hardware such as an ASIC, or as program instructions carried out by a microprocessor or other computing device.

The claims should not be read as limited to the described order of elements unless stated to that effect. In addition, use of the term "means" in any claim is intended to invoke 35 U.S.C. §112, paragraph 6, and any claim without the word "means" is not so intended. Therefore, all embodiments that come within the scope and spirit of the following claims and equivalents thereto are claimed as the invention.

What is claimed is:

1. A patient-controlled system for dispensing medication to a patient at times determined by the patient in an in-patient setting, comprising:

a fingerprint sensor for reading at least a portion of a fingerprint of the patient's finger when the finger is positioned on the fingerprint sensor; a patient activated actuation device operatively associated with the fingerprint sensor;

an encasement connected to the fingerprint sensor and the patient activated actuation device for impeding the ability for a person other than the patient to use the patient's finger to activate the patient activated actuation device;

a microprocessor for receiving data from the fingerprint sensor, the data representing the portion of the fingerprint, and analyzing the data by comparing the fingerprint to a previously stored fingerprint to verify the patient;

a delivery device connected directly to the patient for administering a prescribed amount of the medication to the patient based on the activation of the patient activated actuation device by the patient and verification of the patient;

and a sensor for providing a signal to the microprocessor to prevent the dispensing of medication responsive to detecting that the encasement is not connected to the fingerprint sensor such that the encasement is no longer impeding the ability for a person other than the patient to use the patient's finger to activate the patient activated actuation device.

2. The system of claim 1, further comprising a container for holding the medication wherein the container is associated with the delivery device.

3. The system of claim 1 wherein the delivery device comprises an electronically controlled pump.

4. The system of claim 1 wherein the medication is analgesic.

5. The system of claim 1, further comprising a memory unit for storing the previously stored fingerprint.

6. The system of claim 5, wherein the memory unit is located at the device.

7. The system of claim 5, wherein the memory unit is located on a network that is accessible by the device.

8. The system of claim 1, further comprising a memory unit for storing historical data related to the use of the device for said verification of the patient.

9. The system of claim 1, wherein the delivery device is configured to not administer the prescribed amount of medication when the patient is not verified.

10. The system of claim 1, wherein the delivery device is configured to not administer the prescribed amount of medication during a lockout period.

11. The system of claim 1 wherein the fingerprint sensor is disposable.

12. The system of claim 1 wherein the encasement is formed of a rigid material.

13. The device of claim 1 wherein the encasement requires that the patient insert a substantial portion of the patient's finger into the encasement to activate patient activated actuation device.

14. The system of claim 13 wherein the encasement prevents a person other than the patient from bending the patient's finger in the encasement to activate the patient activated actuation device.

15. The system of claim 13 wherein the encasement requires that the patient bend the patient's finger to activate the patient activated actuation device.

16. The system of claim 15 wherein the encasement requires that the patient bend the patient's finger at the distal interphalangeal joint.

17. The system of claim 1 further comprising a transparent film located inside of the encasement and over the fingerprint sensor.

18. The system of claim 17 wherein the transparent film is disposable.

19. The system of claim 1 wherein the encasement is disposable.

20. The system of claim 1, wherein the patient activated actuation device comprises a pushbutton.

21. The system of claim 20 wherein the pushbutton comprises a pressure sensitive button.

22. The system of claim 21 wherein the pressure sensitive button activates the fingerprint sensor.

23. The system of claim 1 wherein the delivery device is connected to the patient to administer medication intravenously to the patient.

24. The system of claim 1 wherein the encasement further comprises a stop that requires the patient to bend the patient's finger in the encasement to activate the patient activated actuation device.

25. The system of claim 1 wherein the encasement is removable from the fingerprint sensor.

26. A patient-controlled method for dispensing medication to a patient at times determined by the patient in an in-patient setting, comprising:

reading at least a portion of a fingerprint of a finger of the patient when the finger is positioned in an encasement that requires the patient to bend the finger to activate a fingerprint sensor and that impedes the ability of a person other than the patient from using a finger of the patient to activate the fingerprint sensor;

receiving a signal from an actuation device operatively associated with the fingerprint sensor when the actuation device is activated by the finger of the patient;

receiving data from the fingerprint sensor, the data representing the portion of the fingerprint, and analyzing the data by comparing the fingerprint to a previously stored fingerprint to verify the patient;

administering a prescribed amount of the medication directly through a device connected to the patient based on the receipt of the signal from the actuation device and verification of the patient; and declining to administer the prescribed amount of medication if the encasement is not connected to the fingerprint sensor such that the encasement no longer impedes the ability of a person other than the patient from using a finger of the patient to activate the fingerprint sensor.

27. The method of claim 26, wherein the actuation device is a pushbutton.

28. The method of claim 26, further comprising the step of recording the patient's fingerprint and storing data associated with the fingerprint.

29. The method of claim 28, wherein storing the fingerprint comprises storing the data associated with the fingerprint in a memory unit that is located at the device.

30. The method of claim 28, wherein storing the fingerprint comprises storing the data associated with the fingerprint in a memory unit that is located on a network that is accessible by the device.

31. The method of claim 26, further comprising the step of storing historical data related to the use of the device for said verification of the patient.

32. The method of claim 26, further comprising the step of initiating an alert.

33. The method of claim 26 wherein the prescribed amount of the medication is administered to the patient only when the signal is received outside of a lockout period.

34. The method of claim 26 further comprising the step of declining to administer the prescribed amount of medication to the patient if the patient is not verified.

35. The method of claim 26 further comprising the step of declining to administer the prescribed amount of medication to the patient if the signal is received within a lockout period.

36. The method of claim 26 wherein the medication comprises analgesic.

37. The method of claim 26 wherein the step of administering a prescribed amount of medication comprises administering the medication intravenously to the patient.

38. A patient-controlled apparatus for dispensing pain medication to a patient at times determined by the patient in an in-patient setting, comprising:
- a fingerprint sensor with attached encasement for reading at least a portion of a fingerprint of the patient's finger when the finger is positioned in the attached encasement connected to the fingerprint sensor that requires that the patient bend the finger to activate the fingerprint sensor and that impedes the ability of a person other than the patient from using a finger of the patient to activate the fingerprint sensor;
- a patient activated actuation device operatively associated with the fingerprint sensor;
- a device for receiving data from the fingerprint sensor, the data representing the portion of the fingerprint, and analyzing the data by comparing the fingerprint to a previously stored fingerprint to verify the patient;
- an electronically controlled pump for administering a prescribed amount of the pain medication intravenously to the patient upon verification and receipt of a signal from the patient activated actuation device and if outside of a programmed time interval; and
- a sensor for detecting when the attached encasement is not connected to the fingerprint sensor such that the attached encasement no longer impedes the ability of a person other than the patient from using a finger of the patient to activate the fingerprint sensor, and then providing a signal to the electronically controlled pump to prevent the dispensing of medication the fingerprint sensor.

\* \* \* \* \*